United States Patent [19]

DeVries et al.

[11] Patent Number: 5,138,081
[45] Date of Patent: Aug. 11, 1992

[54] PROCESS FOR PURIFYING VINYLICALLY-UNSATURATED ORGANOSILICON COMPOUNDS

[75] Inventors: Robert A. DeVries; Mary L. Ash, both of Midland; Hughie R. Frick, deceased, late of Midland, all of Mich., by Bonnie Frick, administrator

[73] Assignee: The Dow Chemical Company, Midland, Mich.

[21] Appl. No.: 694,521

[22] Filed: Apr. 30, 1991

[51] Int. Cl.$^5$ .............................................. C07F 7/20
[52] U.S. Cl. ................................................... 556/466
[58] Field of Search ........................ 556/466; 210/656

[56] References Cited

U.S. PATENT DOCUMENTS

| | | | |
|---|---|---|---|
| 3,922,299 | 11/1975 | Heck | 260/476 R |
| 4,540,763 | 9/1985 | Kirchhoff | 526/281 |
| 4,622,375 | 11/1986 | Wong | 526/284 |
| 4,724,260 | 2/1988 | Kirchhoff et al. | 546/112 |
| 4,759,874 | 7/1988 | Gros | 252/512 |
| 4,774,347 | 9/1988 | Marko et al. | 556/466 |
| 4,812,588 | 3/1989 | Schrock | 556/453 |
| 4,822,930 | 4/1989 | Liu | 570/206 |
| 4,831,172 | 5/1989 | Hahn et al. | 556/419 |
| 4,956,486 | 9/1990 | Marko et al. | 556/466 |
| 4,962,221 | 10/1990 | Huntress et al. | 556/466 X |

OTHER PUBLICATIONS

Munakata et al., *Chem. Abs.*, 86:55073g (1977).
Collin et al., *Chem. Abs.*, 96:122005h.
Swern, ed., "Organic Peroxides," Krieger Publishing Co., vol. 3 (1981), pp. 236-238.
Horner et al., "Die Reduktion organischer Peroxyde mit tertiären Phosphinen," *Annalen*, vol. 591 (1955) pp. 138-152.
Heck, *Organic Reactions*, vol. 27 (1982), pp. 345-390.
Dieck et al., *J. Am. Chem. Soc.*, vol. 96, pp. 1133-1136 (1973).
Goodyear, Jr., *Chem. Abs.* 54:16381g (1960).
Petrarch Systems, Inc. "Silicon Compounds Register and Review," (1987), p. 114.

*Primary Examiner*—Arthur C. Prescott
*Attorney, Agent, or Firm*—Charlotte M. Kraebel; Charles J. Enright

[57] ABSTRACT

A process for purifying an impure vinylically-unsaturated organosilicon product compound prepared by reaction between a vinylically-unsaturated organosilicon precursor and a halogenated organic compound in the presence of a homogeneous zerovalent palladium catalyst complex, the catalyst complex including an organophosphine or organoarsine ligand, in the presence of a hydrogen halide acceptor in an essentially anhydrous diluent, comprising treating a mixture containing the impure vinylically-unsaturated organosilicon product compound with a peroxide for a time sufficient to oxidize organophosphine or organoarsine impurities present in a mixture being treated. The peroxide can be selected from aqueous hydrogen peroxide or organic peroxides. The thus-treated mixture can be further treated by chromatography over silica gel or alumina. In optional embodiments, chromatography over silica gel or alumina can precede treatment with the peroxide.

42 Claims, No Drawings

PROCESS FOR PURIFYING VINYLICALLY-UNSATURATED ORGANOSILICON COMPOUNDS

TECHNICAL FIELD

This invention relates to an improved process for purifying vinylically-unsaturated organosilicon compounds, prepared by reactions using a palladium-organoarsine or palladium-organophosphine catalyst in an anhydrous solvent, by treating a mixture containing the organosilicon compound with a peroxide to oxidize organophosphine or organoarsine present in the mixture.

BACKGROUND ART

Munakata et al., *Chem. Abs.* 86:55073 g (1977) have recited preparing bis(octaidenyl) 1,2-cyclohexanedicarboxylates by reaction between active hydrogen-containing compounds or carboxylic acid anhydrides and 1,3-dienes, in the presence of Pd compounds and phosphines. The resulting reaction mixtures are treated with peroxides and then with hydrogen and/or carbon monoxide to reduce palladium compounds and remove palladium.

Collin et al., *Chem. Abs.* 96:122005 h, have recited reacting an alpha-olefin, tert-butyl hydroperoxide and carbon monoxide, in the presence of a palladium-phosphine mixture, to produce products of both oxidation and reduction. The mechanism is said to include decomposition of an alkyl-palladium sigma bond by the hydroperoxide.

The interaction of peroxides with organic compounds of Group V elements has been reviewed by Swern, ed., "Organic Peroxides," Krieger Publishing Co., vol. 3 (1981), pages 236–238. Various peroxides are reported to react with $R_3P$ to produce corresponding phosphine oxides. See also, Goodyear, Jr., *Chem. Abs.* 54:16381 g.

Horner et al., "Die Reduktion organischer Peroxyde mit tertiären Phosphinen" *Annalen*, vol. 591 (1955), pages 138–152, consider reduction products from reaction between tertiary phosphines and various organic peroxides.

Vinylically-unsaturated organosilicon compounds are useful as adhesion promoters, particularly for electronic applications. Formulators of adhesives for electronic utilization generally require vinylically-unsaturated organosilicon compounds, containing very low levels of impurities, particularly heavy metal and other inorganic impurities. Organosilicon compounds frequently contain heavy metals, halogens, alkali metals and phosphorus. Any of these materials, in amounts greater than about 1–10 ppm, can cause objectionable properties in adhesive formulations, containing vinylically-unsaturated organosilicon compounds.

The Heck vinylation reaction has been used to vinylate various kinds of compounds, including vinylically-unsaturated organosilicon compounds. The preparation of polysiloxane-bridged bisbenzocyclobutene monomers has been recited by Gros, U.S. Pat. No. 4,759,874, and Schrock, U.S. Pat. No. 4,812,588, both herein incorporated by reference. Schrock '588 discloses chromatography of a product from 4-bromobenzocyclobutene and 1,1'-divinyltetramethyldisiloxane over silica gel. Other silane-containing compounds have been synthesized by Hahn et al., U.S. Pat. No. 4,831,172, herein incorporated by reference. Kirchhoff et al., U.S. Pat. No. 4,724,260, herein incorporated by reference, have prepared an acetylenically-unsaturated organosilicon compounds from 4-bromobenzocyclobutene and trimethyl silylacetylene, using bistriphenylphosphine palladium (II) chloride and cuprous iodide catalysts and triethylamine as hydrogen halide acceptor.

The palladium-catalyzed vinylation of organic halides has been reviewed by Heck, *Organic Reactions*, vol. 27 (1982), beginning at page 345. Process conditions, recited at page 360, do not require the use of a solvent, although an organic amine can apparently function as a solvent. Other solvents used heretofore include acetonitrile, methanol, dimethylformamide, N-methylpyrrolidinone and hexamethyl phosphoramide.

Heck, U.S. Pat. No. 3,922,299, incorporated herein by reference, teaches that the reaction can be carried out with or without a solvent. Suggested solvents include acetonitrile, tetrahydrofuran or excess olefin.

It is therefore the object of this invention to provide an improved process for purification of vinylically-unsaturated organosilicon compounds to produce materials with very low levels of inorganic impurities, which are suitable for electronic applications.

DISCLOSURE OF INVENTION

This invention relates to a process for purifying vinylically-unsaturated organosilicon product compounds, prepared by reaction between a vinylically-unsaturated organosilicon precursor compound and a halogenated organic compound in the presence of a homogeneous zerovalent palladium catalyst complex, the catalyst complex including an organophosphine or organoarsine ligand, in the presence of a hydrogen halide acceptor in an essentially anhydrous diluent, comprising treating a mixture containing the impure vinylically-unsaturated organosilicon product compound with a peroxide for a time sufficient to oxidize organophosphine or organoarsine impurities present in the mixture being treated.

It has surprisingly been found that both organic peroxides and aqueous hydrogen peroxide can be used.

DETAILED DESCRIPTION OF THE INVENTION

Depending upon the process by which vinylically-unsaturated organosilicon compounds are made, products can contain significant amounts of halogens, alkali metals, heavy metals or phosphorus. For example, 1-(4-benzocyclobutenyl)-2-triethoxysilyl)ethylene, isolated by distillation, contains 69 ppm of Br, 3 ppm of Cl and 280 ppm of P. 1-(4-Benzocyclobutenyl)-2-(trimethylsilyl) acetylene, prepared from 4-bromobenzocyclobutene and trimethylsilylacetylene in a reaction mixture containing palladium (II) chloride, cuprous iodide, triphenylphosphine and triethylamine, contains high levels of Pd, Cu, Br and I. These levels of impurities are unacceptable for electronics applications, although the reaction between halogenated organic compounds and vinylically-unsaturated organosilicon compounds in the presence of a zerovalent palladium catalyst complex, in which is included an organophosphine or organoarsine ligand, in an essentially anhydrous diluent is otherwise a feasible route to vinylically-unsaturated organosilicon compounds.

The reaction between halogenated organic compounds and hydrolytically-stable, vinylically-unsaturated organosilicon precursor compounds is carried out in the presence of a zerovalent palladium catalyst complex. The catalyst complex can be added to the reaction mixture or can be formed in the reaction mixture. Representative preformed catalyst complexes include tetrakis-(triphenylphosphine)palladium (0), tris(-dibenzylideneacetone)dipalladium (0) with triphenylphosphine and dichloro(triphenylphosphine)palladium (II).

The catalyst complex can be prepared in the reaction mixture, generally by reaction between a palladium (II) compound and a trivalent organophosphorus or organoarsenic compound.

The reaction between the vinylically-unsaturated precursor compound and halogenated organic compound, in the presence of a representative palladium complex, can be represented by the general equation:

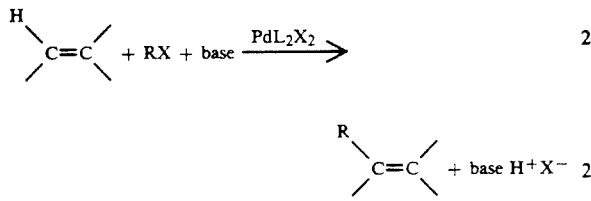

wherein R is aryl, heterocyclic, vinylic or benzyl and X is bromo, iodo or, rarely, chloro. L represents a ligand, which is a trivalent organophosphorus or organoarsenic compound. The base in the equation corresponds to the hydrogen halide acceptor.

Representative ligands in the Pd catalytic complex include, but are not limited to, triphenylarsine, tri-(n-butyl)phosphine, diphenylmethylphosphine, diphenylmethoxyphosphine, triphenylphosphine, triethylphosphine, phenyldi-(n-butoxy)phosphine, tris-(p-anisyl)phosphine and tris-(o-tolyl)phosphine.

Palladium is introduced into the reaction mixture in the form of a salt, such as the acetate or chloride. It is postulated that the catalyst complex should contain two phosphine or arsine ligands per palladium atom.

Catalysts, or catalytic complexes, formed from palladium (II) acylates, particularly Pd(II) acetate, and triaryl phosphines have been found to be particularly preferred for the practice of this invention. Particularly preferred triaryl phosphines are triphenylphosphine and tris-(o-tolyl)phosphine.

Most preferred catalysts are those obtained from Pd (II) acetate and tris-(o-tolyl)phosphine.

The ratio of palladium (II) compound to phosphorus or arsenic ligand can be varied from about 1:1 to about 1:100. It is preferred to operate at ratios of from about 1:2 to about 1:10, particularly when a catalyst from Pd (II) acetate and tris-(o-tolyl)phosphine is used.

The amount of catalyst complex is varied from about 0.1 mol to 0.00001 mol (as Pd) per mol of halogenated organic compound in the reaction mixture. Preferably, the catalyst level is 0.01–0.00001 mol (as Pd) per mol of halogenated organic compound.

The mixture being treated with a peroxide can be the crude reaction mixture, containing the essentially anhydrous diluent. The mixture can contain an additional organic solvent, e.g. methanol, ethanol or heptane.

The amount of peroxide is at least that necessary to oxidize any organophosphine or organoarsine to a corresponding arsine oxide or phosphine oxide. The peroxide can be added incrementally, either in portions or using a metering pump to add a solution of the peroxide. It will be understood that it may be preferable to avoid an exothermic reaction during the treatment with a peroxide and that the rate at which peroxide is added can be determined by routine experimentation.

The mixture, containing the peroxide, is stirred at room temperature or at an elevated temperature, up to the boiling point of the solvent or diluent in the mixture until conversion to phosphine or arsine oxide is complete. The treatment with peroxide is conveniently carried out under ambient pressure. However, the reaction can be carried out in a pressure vessel at pressures, greater than atmospheric. The optimum pressure and temperature conditions for use with a given reaction mixture and selected peroxide can be determined by routine experimentation.

The treated product can be filtered, if necessary, to remove any solid residues resulting from the treatment. Solvent can be removed from the mixture at this point, or the solution can be applied directly to a packed column of silica gel or alumina.

Most preferably a solution of the organosilicon product mixture is applied to the column and elution is carried out using a hydrocarbon solvent, such as heptane or petroleum ether. Solvent is removed from the eluate be evaporation using conventional techniques. The amount of silica gel or alumina used to pack the chromatography column can be determined by routine experimentation.

Silica gels and alumina, suitable for chromatography, are commercially available, for example, Fisher basic alumina (80–200 mesh, Brockman Activity 1), Baker chromatography grade silica gel (80–230 Å) and Davison Chemical chromatographic grade 62 silica (60×200 mesh). Standard techniques for packing the chromatography column can be used.

Vinylically-unsaturated organosilicon compounds treated with a peroxide and then by chromatography over silica gel or alumina have very low inorganic impurity levels, for example, below 1 ppm of Pd or P.

Alternatively, the impure vinylically-unsaturated organosilicon compounds can be chromatographed over silica gel or alumina and then treated with a peroxide. An additional filtration step of treatment by column chromatography may be required to reduce impurities to acceptable levels.

The hydrogen halide acceptor, used in the practice of this invention, can be selected from inorganic bases or amines, as disclosed by Heck, supra. It is preferred to use amines as hydrogen halide acceptors, preferably a secondary or tertiary amine. Representative secondary and tertiary amines include, but are not limited to, trimethylamine, triethylamine, methylethylamine, diethyl-n-butylamine, triisobutylamine, tri-n-butylamine, diisopropylamine, triisopropylamine, N,N,N',N'-tetramethylethylene diamine, N-methylcyclohexylamine, N,N-diethylcyclohexylamine, N,N-diethylaniline, N,N-dimethylaniline, N-methyltoluidine, pyridine, quinoline, the lutidines, N-methylpiperidine, N-methylpyrrole and the like.

Preferred hydrogen halide acceptors are tertiary amines, particularly those represented by the formula $R_1R_2R_3N$, wherein each of $R_1$, $R_2$ and $R_3$ is selected independently from straight-chain and branched-chain alkyl of 1–8 carbon atoms and cycloalkyl. Most preferably, the hydrogen halide acceptor is triethylamine.

The molar ratio of hydrogen halide acceptor to halogenated organic compound can be varied from about 1:1 to about 10:1. Using greater excesses of organic hydrogen halide acceptor is not particularly advantageous. It has been found that excellent results are obtained using a 1-3 mols of hydrogen halide acceptor per mol of halogenated organic compound. Therefore, preferred ratios of hydrogen halide acceptor to halogenated organic compound are from about 1:1 to about 3:1.

The essentially anhydrous diluent comprises an organic solvent selected from nitriles, alcohols, ketones, linear or cyclic saturated esters, N,N-dialkylformamides, N-alkylpyrrolidinones, alkoxyalkanols, glycol ethers, dioxane, tetrahydrofuran, tetrahydropyran or hexaalkylphosphoramides. It will be understood that "essentially anhdyrous" means that the solvents are of reagent grade or higher purity and that water has not been added to the solvent or reaction mixture. It will further be understood that water can be taken up into the solvent or reaction mixture during handling of the materials involved and that this amount of water is within the scope of materials, defined as being "essentially anhydrous."

Suitable nitriles include, but are not limited to, acetonitrile, propionitrile, butyronitrile, and higher aliphatic nitriles, as well as benzonitrile, tolylnitrile, methoxybenzonitrile, etc. A preferred nitrile solvent is acetonitrile.

Alcohols which can be used include alkanols of 1-8 carbon atoms, including the various isomeric forms.

Esters useful as diluents include linear or cyclic saturated esters, for example, ethyl acetate, methyl propionate, isopropyl butyrate, caprolactone and butyrolactone.

Ketones, useful as diluents, include acetone, methyl ethyl ketone, methyl isopropyl ketone, and similar compounds.

Of the various N,N-dialkylformamides which can be used in as diluents, N,N-dimethylformamide is most preferred.

N-Methylpyrrolidinone is preferred among the various N-alkylpyrrolidinones.

Alkoxyalkanols suitable for use as diluents include those of up to about 10 carbon atoms, e.g. ethylene glycol monomethyl ether, propylene glycol monoethyl ether, ethylene glycol monobutyl ether, propylene glycol monoisopropyl ether, etc.

Glycol ethers, including ethylene glycol dimethyl or diethyl ethers, corresponding propylene glycol ethers, or diethylene glycol or triethylene glycol diethers can also be used.

Of the hexaalkylphosphoramides which can be used in as diluents, hexamethylphosphoramide is preferred.

Preferred diluents are acetonitrile, N,N-dimethylformamide or N-methylpyrrolidinone.

The amount of essentially anhydrous diluent may be varied within wide ranges. Generally, the amount of diluent is 0.5-5 parts by volume with respect to the combined amount of halogenated organic compound, vinylically-unsaturated organosilicon precursor compound and hydrogen halide acceptor.

Halogenated organic compounds, useful as starting materials for the process of this invention, include mono- and polycyclic, substituted or unsubstituted carbocyclic or heterocyclic aromatic bromo and iodo compounds and, rarely, chloro compounds, provided that any substituent is inert under the reaction conditions employed. The reactive halogenated organic compounds can be classified broadly as aryl halides, benzyl halides or vinylic organic halides.

Benzyl halides include substituted and unsubstituted benzyl chlorides, bromides and iodides. The benzyl chlorides are sufficiently reactive to add to a vinylically-unsaturated precursor compound. Benzyl chlorides and halides are preferred reagents for this synthesis. Substituents on the aromatic ring of the starting benzyl halide include straight and branched chain alkyl, alkoxy, nitro, cyano, hydroxy, keto, amide, carboxy, dialkylamino and sulfone groups. It will be understood that 1-halobenzocyclobutenes represent a type of benzyl halide.

Vinylic halides, useful in the practice of this invention include, for example 1- or 2-bromo- or iodoalkenes of the formulas $CH_2=CXR$ or $CHX=CHR$, wherein X is Br or I and R is alkyl or aryl.

Aromatic halides include substituted and unsubstituted aryl bromides and iodides. Aryl chlorides generally are unreative under the conditions used. Substituents on the aromatic ring or rings can include straight and branched chain alkyl, alkoxy, nitro, cyano, hydroxy, ketone, amide, carboxy, dialkylamino or sulfone groups. Aromatic halides include both monocyclic and polycyclic aromatic halides.

Representative heterocyclic reactants include, but are not limited to, bromofuran, bromopyridine, bromo-N-methylpyrrole, iodofuran, iodolutidine, etc.

Preferably, the halogenated organic compound used as feed is selected from bromo- or iodo- mono- or polycyclic substituted or unsubstituted carbocyclic or heterocyclic compounds or substituted or unsubstituted benzyl chlorides or bromides. Bromo compounds are most preferred as starting materials.

Substituents on substituted halogenated carbocyclic aromatic compounds are preferably selected from alkyl of 1-6 carbon atoms, alkoxy of 1-6 carbon atoms, chloro or cyano. It will be appreciated that alkyl and alkoxy substituents can be straight-chain or branched-chain.

A class of preferred reactants includes bromo- or iodo-benzocyclobutenes, as disclosed by Gros, U.S. Pat. No. 4,759,874, supra. Most preferably, the reactant is a brominated benzocyclobutene, represented by the formula

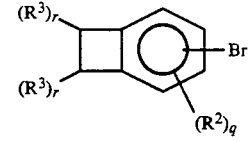

wherein $R^2$ is alkyl of 1-6 carbon atoms, acyloxy of 1-6 carbon atoms, alkoxy of 1-6 carbon atoms, nitro or chloro; each $R^3$ is independently alkyl of 1-6 carbon atoms, aryl, nitro, chloro or cyano; q is 0, 1, 2 or 3 and each r is independently 0 or 1.

Brominated benzocyclobutenes can be prepared as recited by Liu, U.S. Pat. No. 4,822,930, herein incorporated by reference. Most preferably, 4-bromobenzocyclobutene is used in processes of this invention. This starting material is obtained in high purity by distilling materials in accordance with Liu '930.

It will be understood that "benzocyclobutene" is an art-recognized term for a cyclobutarene compound, Liu '930. Cyclobutarene compounds are compounds, containing at least one aromatic ring, which is fused to one or more substituted or unsubstituted cyclobutene ring. An aromatic ring contains (4N+2)n electrons, as described in Morrison and Boyd, *Organic Chemistry*, third edition (1973). In the numbering system for benzocyclobutenes, the 1- and 2-positions are in the cyclobutene ring. The 3- and 6-positions are in an aromatic ring, adjacent to the cyclobutene ring. The 4- and 5-positions are meta- to the cyclobutene ring. Benzocyclobutenes are formally identified as derivatives of bicyclo[4.2.-0]octa-1,3,5-triene. Correlations between various representative names and structures are given in Table 1.

dimethylvinylsilane, phenylmethylvinylsilane, polyvinylmethylsiloxane, 1,1,3,3-tetravinyldimethyldisiloxane, tetravinylsilane, 1,3,5,7-tetramethylcyclotetrasiloxane, triphenylvinylsilane, tris(vinyldimethylsiloxy)methylsilane, tris(vinyldimethylsiloxy)methylsilane, trivinylmethylsilane and 1,3,5-trivinyl-1,1,3,5,5-pentamethyltrisiloxane, any of which is exemplary of hydrolytically-stable organosilicon compounds, useful in the practice of this invention.

A further group of organosilicon compounds are di- and higher polysiloxanes, represented by the formula

TABLE 1

Structures and Names of Representative Reactants and Products

| Short Name | Structure | Alternative Names |
| --- | --- | --- |
| 4-BrBCB | 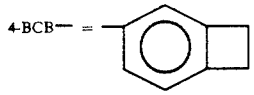 | 3-bromobicyclo[4.2.0]octa-1,3,5-triene<br>4-bromobenzocyclobutene |
| DVS | [H$_2$C=CHSi(CH$_3$)$_2$]$_2$O | 1,1'-divinyltetramethyldisiloxane<br>1,3-divinyltetramethyldisiloxane |
| DVS-BCB$_2$ | [(4-BCB—CH=CH)—Si(CH$_3$)$_2$]$_2$O | 1,1'-bis-[(4-benzocyclobutenyl)vinyl]tetramethyldisiloxane<br>1,3-bis-(2-bicyclo[4.2.0]octa-1,3,5-trien-3-ylethenyl)-1,1,3,3-tetramethyldisiloxane |
| DVS-BCB | 4-BCB—CH=CH—Si(CH$_3$)$_2$OSi(CH$_3$)$_2$CH=CH$_2$ | 1-[(4-benzocyclobutenyl)vinyl]-1'-vinyltetramethyldisiloxane |
| TMS-BCB | 4-BCB—CH=CH—Si(OCH$_3$)$_3$ | 4-[2-(trimethoxysilyl)-vinyl]-benzocyclobutene<br>1-(4-benzocyclobutenyl)-2-(trimethoxysilyl)ethylene |

4-BCB— = 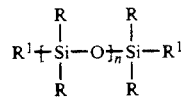

Preferred halogenated organic compounds include brominated and iodinated alkylbenzenes and alkylnapthalenes or corresponding alkoxy compounds, wherein alkyl and alkoxy are of 1–6 carbon atoms and can be of any isomeric structure. A particularly preferred halogenated organic compound is of the formula ArBr, wherein Ar is substituted or unsubstituted monocyclic aromatic. Most preferred as a halogenated organic compound is that wherein Ar is phenyl or o-, m- or p-tolyl, or a mixture thereof.

Also preferred as halogenated organic compounds are substituted or unsubstituted benzyl chlorides or bromides, particularly those wherein the substituent is alkyl or alkoxy of 1–6 carbon atoms.

Vinylic iodides or bromides are also preferred.

Vinylically-unsaturated organosilicon precursor compounds employed in the process of this invention can be selected from those containing vinyl, allyl, ethynyl or methallyl moieties. The process of this invention is applicable to vinylically-unsaturated organosilicon compounds, regardless of their hydrolytic stability.

Organosilicon compounds are commercially available. A representative source is Petrarch Systems, Inc., Bartram Road, Bristol, Pa., 19007.

Hydrolytically-unstable organosilicon compounds, available from Petrarch, include vinyltriacetoxysilane (CV4800), vinyltriethoxysilane (CV4910), vinyltrimethoxysilane (CV4917), vinyltris(methoxyethoxy)silane (CV5000) and vinyltris-(1-methoxyl-2-propoxy)silane (CV5010).

Petrarch's "Silicon Compounds Register and Review," (1987), page 114, recites the availability of bis(-dimethylamino)methylvinylsilane, 1-bromo-vinyltrimethylsilane, tert.-butyldimethylvinylsilane, divinyldimethylsilane, 1,3-divinyl-1,3-diphenyl-1,3-dimethyldisiloxane, 1,3-divinyl-1,3-diphenyl-1,3-dimethyldisilazane, 1,3-divinyl-1,1,4,4-tetramethyldisilylethylene, phenyl- $$R^1 \!\!+\!\! \underset{\underset{R}{|}}{\overset{\overset{R}{|}}{Si}} \!\!-\!\! O\!\!\underset{n}{\!\!\!\!\!\!\!\!\!\!\!\!\!\!\!\!\!\!\!\!\!\!\!\!\!\!]}\!\! \underset{\underset{R}{|}}{\overset{\overset{R}{|}}{Si}} \!\!-\!\! R^1$$

wherein each R is independently alkyl of 1–6 carbon atoms, cycloalkyl, aralkyl or aryl; each $R^1$ is independently vinyl, allyl or methallyl; and n is an integer from 1 to 4500.

Most preferably, $R^1$ is vinyl and each R is methyl, ethyl or phenyl. Preferred siloxanes are those wherein n is 2–10. Several of these compounds are available from Petrarch Systems, above. A most preferred member of this group of compounds is 1,1'-divinyltetramethyldisiloxane, represented by the formula [CH$_2$=CHSi(CH$_3$)$_2$]$_2$O.

The process of this invention is preferably applied to products, obtained from organosilicon compounds in which a vinyl, allyl, methallyl or ethynyl moiety is bonded directly to silicon. The process is preferably applied to materials obtained by reaction with trialkoxyvinylsilanes, in which alkoxy is of 1–6 carbon atoms, including various isomeric forms. Most preferably, the process of this invention is applied to products from trimethoxyvinylsilane or triethoxyvinylsilane.

Most preferred products, obtained by the process of this invention, are those prepared from:

(a) 4-bromobenzocyclobutene and trimethoxyvinylsilane, (b) 4-bromobenzocyclobutene and triethoxyvinylsilane, (c) 4-bromobenzocyclobutene and trialkoxysilane, wherein alkoxy is of 1–6 carbon atoms and (d) 4-bromobenzocyclobutene and triacetoxyvinylsilane.

The molar ratio of halogenated organic compound to vinylically-unsaturated organosilicon precursor compound can be determined by routine experimentation. Generally, molar ratios of about 0.5:1 to 1.5:1 will be preferred for the synthesis of monoadducts. Higher molar ratios of halogenated organic compound to vinylically-unsaturated organosilicon precursor will be employed when higher adducts are being prepared.

The temperature at which the process of this invention is performed can be from about room temperature to the temperature at which the starting materials or products decompose or polymerize. Elevated temperatures are normally preferred for the vinylation reaction. It has been found that heating under reflux, generally at 80°-120° C., usually permits a reasonable reaction rate. The temperature conditions for a given set of reactants and diluent can readily be ascertained by routine experimentation.

Aqueous hydrogen peroxide can be used for oxidation of organophosphine residues to phosphine oxides. The crude product is treated with aqueous hydrogen peroxide at ambient or somewhat elevated temperatures for a time sufficient to oxidize residual phosphine to phosphine oxide. The use of aqueous hydrogen peroxide is preferred when the organosilicon product is relatively stable to hydrolysis.

When the organosilicon product is relatively unstable to hydrolysis, oxidation of phosphine residues is preferably done using an organic peroxide. Preferred organic peroxides include hydroperoxides, peresters and peracids, of which tert-butyl hydroperoxide, cumeme hydroperoxide, perbenzoic acid, m-chloroperbenzoic acid, monoperphthalic acid and peracetic acid are representative. tert-Butyl hydroperoxide is preferred. Treatment with an organic peroxide can be done at ambient temperature or at temperatures up to 80°-90° C.

It is preferred to purify the crude reaction products by chromatography over silica gel or alumina. This accomplishes removal of palladium residues and, when used after treatment of a crude product with a peroxide, also removes phosphine oxide.

When ultrapure, ionic-free, reaction products are required, as for adhesion promoters in electronic applications, it is preferred to treat crude reaction products with aqueous hydrogen peroxide or tert-butyl hydroperoxide and to chromatograph the crude products over silica or alumina. These purification steps can be carried out in either order.

Accordingly, preferred processes of this invention are those wherein:

(a) the halogenated organic compound is a bromo or iodo mono- or polycyclic substituted or unsubstituted carbocyclic or heterocyclic compound or a substituted or unsubstituted benzyl chloride, bromide or iodide;

(b) the halogenated organic compound is a brominated benzocyclobutene represented by the formula

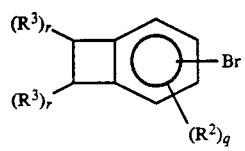

wherein $R^2$ is alkyl of 1-6 carbon atoms, alkoxy of 1-6 carbon atoms, trifluoroacetoxy, acyloxy of 1-6 carbon atoms, nitro or chloro; each $R^3$ is alkyl of 1-6 carbon atoms, aryl, nitro, chloro or cyano; q is 0, 1, 2 or 3 and each r is independently 0 or 1;

(c) the halogenated organic compound is 4-bromobenzocyclobutene;

(d) the halogenated organic compound is of the formula ArBr, wherein Ar is phenyl or o-, m- or p-tolyl;

(e) the halogenated organic compound is a substituted or unsubstituted benzyl bromide or chloride;

(f) the halogenated organic compound is a vinylic bromide;

(g) the vinylically-unsaturated organosilicon precursor compound is a hydrolytically-unstable ethynyl, vinyl, allyl or methallyl organosilicon compound, including each of (a)-(f);

(h) the vinylically-unsaturated organosilicon precursor compound is a trialkylvinylsilane, wherein alkyl is of 1-6 carbon atoms, including each of (a)-(f);

(i) the vinylically-unsaturated organosilicon precursor compound is of the formula

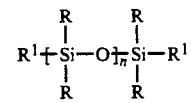

wherein each R is independently alkyl of 1-6 carbon atoms, cycloalkyl, aralkyl or phenyl; each $R^1$ is independently vinyl, allyl or methallyl and n is an integer from 1 to 4500, including each of (a)-(f);

(j) the vinylically-unsaturated organosilicon precursor compound is $[CH_2=CH-Si(CH_3)_2]_2O$, including each of (a)-(f);

(k) the vinylically-unsaturated organosilicon precursor compound is a trialkoxyvinylsilane, wherein alkoxy is of 1-6 carbon atoms, including each of (a)-(f);

(l) the vinylically-unsaturated organosilicon precursor compound is trimethoxyvinylsilane, including each of (a)-(f)

(m) the vinylically-unsaturated organosilicon precursor compound is triethoxyvinylsilane, including each of (a)-(f);

(n) the vinylically-unsaturated organosilicon precursor compound is triacetoxyvinylsilane, including each of (a)-(f);

(o) the vinylically-unsaturated organosilicon product compound is a reaction product of 4-bromobenzocyclobutene and trimethoxyvinylsilane;

(p) the vinylically-unsaturated organosilicon product compound is a reaction product of 4-bromobenzocyclobutene and triethoxyvinylsilane;

(q) the vinylically-unsaturated organosilicon product compound is a reaction product of 4-bromobenzocyclobutene and triacetoxyvinylsilane;

(r) the vinylically-unsaturated organosilicon product compound is a reaction product of 4-bromobenzocyclobutene and 1,1'-divinyl-tetramethyldisiloxane;

(s) the catalyst complex is formed from palladium (II) acetate and a triarylphosphine, including each of (a)-(r);

(t) the catalyst complex is formed from a palladium (0) complex and a triarylphosphine, including each of (a)-(r);

(u) the catalyst complex is formed from palladium (II) acetate and tris-(o-tolyl)phosphine, including each of (a)-(r);

(v) the hydrogen halide acceptor is a secondary or tertiary amine, including each of (a)-(u);

(w) the hydrogen halide acceptor is represented by the formula $R_1R_2R_3N$ and each of $R_1$, $R_2$ and $R_3$ is selected independently from straight-chain and branched-chain alkyl of 1–8 carbon atoms and cycloalkyl, including each of (a)–(u);

(x) the hydrogen halide acceptor is triethylamine, including each of (a)–(u);

(y) the anhydrous diluent is present in amount exceeding 100% by weight of combined halogenated organic compound, vinylically-unsaturated organosilicon precursor compound and hydrogen halide acceptor, including each of (a)–(x);

(z) the anhydrous diluent is organic solvent selected from the group consisting of nitriles, alcohols, linear or cyclic saturated esters, N,N-dialkylformamides, N-alkylpyrrolidinones, alkoxyalkanols, glycol ethers, ketones, dioxane, tetrahydrofuran, tetrahydropyran or hexaalkylphosphoramides, including each of (a)–(x);

(aa) the anhydrous diluent is N,N-dimethylformamide or N-methylpyrrolidinone, including each of (a)–(x);

(bb) the anhydrous diluent is acetonitrile, including each of (a)–(x);

(cc) the peroxide is aqueous hydrogen peroxide, including each of (a)–(bb);

(dd) the peroxide is tert-butyl hydroperoxide, including each of (a)–(bb); and (ee) a further step of chromatographing a resulting crude product over silica gel or alumina is included, including each of (a)–(dd).

BEST MODE FOR CARRYING OUT THE INVENTION

Most preferred products, prepared by the process of this invention are those prepared from:

(a) 4-bromobenzocyclobutene and trimethoxyvinylsilane and (b) 4-bromobenzocyclobutene and triethoxyvinylsilane.

A most preferred catalyst complex is that formed from palladium (II) acetate and tris-(o-tolyl)phosphine.

A most preferred diluent is acetonitrile.

Most preferably, a resulting crude product is treated with tert-butyl hydroperoxide.

SPECIFIC EMBODIMENTS

Without further elaboration it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following examples, the temperatures are set forth uncorrected in degrees Celsius. Unless otherwise indicated, all parts and percentages are by weight.

EXAMPLE 1

Coupling of 4-BrBCB and Trimethoxyvinylsilane to Produce 4-[2-(Trimethoxysilyl)vinyl]-benzocyclobutene; in Acetonitrile Into a 5-L, three-necked round-bottom flask, fitted with a reflux condenser, thermowell and air-driven polytetrafluoroethylene stirring shaft, is charged 480.9 g (2.628 mol) of 4-bromobenzocyclobutene, 388.9 g (2.628 mol) of trimethoxyvinylsilane, 530.9 g (5.256 mol) of triethylamine, 1.77 g (0.0079 mol) of palladium (II) acetate, 9.61 g (0.0315 mol) of tris-(o-tolyl)phosphine and 1600 mL of acetonitrile.

The resulting mixture is stirred and heated under reflux for 24 h, after which a distillation head is added to the round-bottom flask and about 1300 mL of acetonitrile is removed. Toluene is added to the resulting pot resulting pot residue in three 500-mL portions. Additional acetonitrile is removed by distillation after each addition of toluene.

After all of the acetonitrile is removed, the resulting slurry is cooled to ambient temperature. Stirring is discontinued and 2500 mL of deionized water is added to the mixture. The aqueous phase is removed and the toluene phase is washed with three 2000-mL portions of deionized water.

The washed toluene phase is passed through a column containing 150 g of silica gel and 50 g of magnesium sulfate. Toluene is removed from the column effluent in vacuo to give 634.1 g (96.5% of theory) of crude 4-[2-(trimethoxysilyl)vinyl]benzocyclobutene. Flash distillation of the crude product gives 512 g (80.1%) of 4-[2-(trimethoxysilyl)vinyl]benzocyclobutene (TMS-BCB), distilling from 110°–111° C. at 0.35 mm Hg.

The flash-distilled TMS-BCB (512 g) and 1 L of heptane are charged to a 5-L round-bottom flask, equipped with an air-driven polytetrafluoroethylene stirrer, thermowell and condenser. The untreated material contains 92 ppm of phosphorus (X-ray fluorescene). To the stirred solution is added 125 mL of 30% hydrogen peroxide. Stirring is continued for 6.5 h.

The aqueous phase is removed and the organic phase is washed with five 500-mL portions of deionized water. After the fifth water wash, the level of peroxide in the aqueous layer is less than 5 ppm.

The resulting organic layer is passed through a column packed with 150 g of silica gel and 50 g of magnesium sulfate. The eluate contains 9 ppm of phosphorus (X-ray fluorescence).

Solvent is removed in vacuo from column effluent to give 476.6 g of product (93.1% recovery).

Flash distillation gives 401.8 g (61.1% overall yield) of purified 4-[2-(trimethoxysilyl)vinyl]benzocyclobutene, b.p. 94°–96° C. at 0.23 mm Hg.

NMR (CDCl$_3$) δ7.0–7.45 (m, 5H), 5.8–6.2 (d, 2H), 3.6 (s, 9H), 3.1 (s, 4H).

EXAMPLE 2

(a) Preparation of 4-[2-(Triethoxysilyl)vinyl]benzocyclobutene

The following reagents are used:

| | |
|---|---|
| 451 g | 4-bromobenzocyclobutene (2.467 mol, Dow) |
| 469.5 g | triethoxyvinylsilane (2.467 mol, 500-mL bottle, Aldrich Chemical Co.) |
| 498.3 g | triethylamine (4.934 mol, Fisher, reagent grade) |
| 1.66 g | palladium (II) acetate (Engelhard) |
| 9.01 g | tris-(o-tolyl)phosphine (0.0296 mol, Strem Chemical Co.) |
| 1500 mL | acetonitrile (Fisher, HPLC grade) |

To a 5-L glass reactor, equipped with a stirrer, reflux condenser and thermometer well, are charged half of the acetonitrile, triethoxyvinylsilane, palladium acetate, tris-(o-tolyl)phosphine and bromobenzocyclobutene. The remaining acetonitrile (750 mL) is added.

The resulting solution is purged with a stream of nitrogen for at least 30 min, after which the triethylamine is added and the solution is heated to reflux. The mixture was stirred and heated under reflux for about 20 h, at the end of which the mixture is checked by GC. Testing was continued at hourly intervals until no BrBCB was detected in the GC output. This required 24 h, at which point the reaction is considered complete.

The reaction mixture is cooled to 70° C. and the condenser is removed and replaced by a distillation head. The contents of the flask are heated under reflux and acetonitrile and unreacted triethylamine are removed by distillation, during the course of which 1000 mL of toluene is added to the reaction vessel.

At the end of the distillation, the reaction mixture is allowed to cool to 50° C. and stirring is stopped to permit precipitated triethylammonium bromide to settle to the bottom of the mixture. Deionized water (1000 mL) is added to the mixture without stirring and a resulting aqueous (bottom) layer is discarded. An additional 1000 mL of water is added and a resulting aqueous layer is discarded.

The organic layer is washed with seven 1000-mL portions of deionized water by adding each portion of water to the reactor and stirring gently for 1 min, stopping stirring and allowing an aqueous layer to separate and removing the resulting aqueous layer. The pH of the aqueous layer is monitored. Washing is complete when the pH of the aqueous layer is 7.

The organic layer is filtered through 300 g of silica gel and 50 g of magnesium sulfate, after which the column is washed with 1000 mL of toluene. The combined eluate and washings are evaporated in vacuo to give 640 g of crude 4-[2-(triethoxysilyl)vinyl]benzocyclobutene (TES-BCB).

(b) Purification

Crude TES-BCB (835 g, 2.86 mol), containing 0.29 g (0.00096 mol) of tris-(o-tolyl)phosphine by 0.43 g of tert.-butyl hydroperoxide (0.0048 mol) and 400 mL of hexane are charged to a 5-L, three-necked flask, fitted with an air-driven stirrer with a polytetrafluoroethylene shaft and paddles, reflux condenser and thermometer well. The solution is stirred and heated to reflux and maintained under reflux conditions for 4 h. The resulting mixture is cooled to 39° C. and filtered through a column packed with 400 g of silica gel and 50 g of magnesium sulfate on a 5-micron nylon filter. The solvent is removed from the effluent in vacuo to give 791 g of TES-BCB, containing 3 ppm of phosphorus.

EXAMPLE 3

(a) Coupling of 4-Bromobenzocyclobutene with Triethoxyvinylsilane

To a 5-L round-bottom flask, equipped with a bottom take-off, reflux condenser, air-driven stirrer, thermowell and nitrogen purge are charged:

| | |
|---|---|
| 480.9 g | 4-bromobenzocyclobutene (2.628 mol, Dow) |
| 500 g | triethoxyvinylsilane (2.628 mol, Aldrich) |
| 530.9 g | triethylamine (5.256 mol, Fisher, reagent grade) |
| 1.77 g | palladium (II) acetate (7.9 mmol, Engelhard) |
| 9.61 g | tris-(o-tolyl)phosphine (31.5 mmol, Strem Chemical Co.) |

The flask is equipped with a heating mantle and the contents are diluted with 1600 mL of acetonitrile (Fisher) and purged with nitrogen for 30 min. The mixture is stirred and heated under reflux and the progress of the reaction is followed by removing samples for GC analysis.

GC is done using Hewlett-Packard 5710 GC with a 3390A integrator using a J & W 30 m narrow-bore capillary column bonded with DB-1, 1.00 micrometer. film thickness. The temperature program is: isothermal at 100° C./2 min, ramp at 8° C./min to 230° C.; hold at 230° C. for 8 or more min.

After 26.5 hours heating under reflux, heating is stopped and the reaction mixture is allowed to cool to 70° C. and transferred to a 3-L Erlenmeyer flask. The resulting precipitate is removed by filtration under vacuum. Acetonitrile and triethylamine are removed from the mother liquors under vacuum and the resulting oil is purified by vacuum distillation. The major product boils at 117°-120° C. at about 0.4 mm Hg. This product weights 632.6 g (82.3%).

The product contains 68 ppm Br, 3 ppm Cl and 280 ppm P by neutron activation analysis.

(b) Treatment with Hydrogen Peroxide to Remove Triarylphosphine

To a 5-L flask equipped with a bottom dump and air-driven polytetrafluoroethylene stirrer is charged 590.3 g of crude product, 1 L of heptane and 400 mL of methanol. Hydrogen peroxide (30%, four 50-mL portions) is added to the stirred mixture at 10-min intervals. After an initial exothermic reaction (about 1°), the mixture is stirred for 4 h at room temperature.

The methanol/peroxide/water layer is removed through the bottom dump and the remaining mixture is washed with four 1200-mL portions of deionized water.

The washed organic layer is passed over a bottom 3.81-cm layer of silica gel (chromatographic silica Grade 62, 60×20 mesh, Davison Chemical, distributed by Fisher Scientific) and top layer of 2.54 cm of magnesium sulfate on a 10.16-cm diameter filter.

Heptane is stripped from the filtrate at 65° C. using a rotary evaporator. The recovered material weights 579.3 g.

(c) Chromatographic Purification

A column (6.35 cm inner diameter, 88.26 cm in height) is packed with silica gel (1010 g, Grade 62, 60×200 mesh, Davison Chemical) suspended in n-heptane. Crude product (579.3 g) is added undiluted to the top of the column and heptane is added until product is on the column. Product is eluted from the column with 8 L of heptane to recover 510 g of product. Residual heptane is removed using a rotary evaporator at 100° C. over 3 h to yield 498 g of pure 4-[2-(triethoxysilyl)-vinyl]benzocyclobutene.

An IR spectrum of the product shows no hydrolysis to silanol.

GC analysis shows higher than 99% purity, including gem-substituents and ring isomers.

The yield of purified product from peroxide treatment and chromatographic purification is 84.4%

The product contains less than 0.2 ppm Na, less than 0.5 ppm Pd, 1.0 ppm Cl, 10 ppm Br and less than 1.0 ppm P by neutron activation analysis.

EXAMPLE 4

(a) Experiments are run as in Example 1, using triphenylphosphine instead of tris-(o-tolyl)phosphine. The catalytic species is believed to be bis(triphenylphosphine)palladium (0). The crude reaction mixture is treated with aqueous hydrogen peroxide, in an amount sufficient to react with triphenylphosphine and the thus-treated material is chromatographed over silica gel. The level of phosphorus is thereby lowered to that acceptable for electronic utilization.

(b) Similar results are obtained, using tributylphosphine as a catalyst component.

(c) Similar results are obtained using as a catalyst component tris(dibenzylideneacetone)dipalladium (0) with triphenylphosphine or dichloro(triphenylphosphine)palladium (II).

EXAMPLE 5

(a) Coupling of 4-Bromobenzocyclobutene and 1,1'-Divinyltetramethyldisiloxane in Acetonitrile A solution of 3.0 g of 4-bromobenzocyclobutene, 1.52 g of 1,1'-divinyltetramethyldisiloxane (DVS), 1.66 g of triethylamine, 0.152 g of tris-(o-tolyl)phosphine, 72 mg of palladium (II) acetate and 10 mL of acetonitrile in a 50 mL-round-bottom flask, equipped with a reflux condenser and magnetic stirring bar, is heated under reflux for 24 h.

At the end of 24 h, the reaction mixture is cooled to room temperature and poured into 60 mL of 10% aqueous hydrochloric acid. The resulting mixture is extracted with two 50-mL portions of methylene chloride and the combined methylene chloride extracts are washed with three 100-mL portions of water.

The organic phase is dried over anhydrous magnesium sulfate, filtered and evaporated in vacuo to yield a yellow oil. The oil is chromatographed on silica gel, using 20% toluene in heptane as eluting solvent. The eluate is evaporated to yield a colorless oil. The product is believed to be a mixture of 1,1'-bis-[(4-benzocyclobutenyl)vinyl]tetramethyldisiloxane (DVS-BCB$_2$) and 1-[(4-benzocyclobutenyl)vinyl]-1'-vinyltetramethyldisiloxane.

(b) Removal of Phosphine Residues from Product

A solution of DVS-BCB$_2$, prepared as in (a) is stirred during the addition of tert-butyl hydroperoxide, in an amount sufficient to react with tris-(o-tolyl)phosphine. The mixture is stirred at 60° C. for 16 h and then cooled to room temperature. A filter is prepared by packing a column of suitable size with 400 g of silica gel and 90 g of magnesium sulfate, on top of a 5 micron filter. The organic solution is passed through the column and the column is washed with 500 mL of Isopar G. The eluate from the column is evaporated to dryness and distilled.

Inorganic impurity content at various points of the purification procedure are:

| ppm | crude | filtered | distilled |
|-----|-------|----------|-----------|
| Br  | 159   | 10       | 1.9       |
| Cl  | 3     | 7        | 3.3       |
| P   | 305   | <2       | <0.3      |
| K   |       | <0.3     |           |
| Na  |       | <0.2     |           |
| Si  | 8.6   | 6.3      |           |

These results show that treatment of the crude product with an organic hydroperoxide produces a product, sufficiently pure for use in electronic applications.

EXAMPLE 6

Evaluation of Organic Oxidizing Agents for Reaction with Phosphines (a) Reaction with Butylene Oxide To a 100-mL round-bottom flask, fitted out with a magnetic stirring bar and condenser, is charged 100 g of hexane, 0.5 g (0.00164 mol) of tris-(o-tolyl)phosphine and 0.236 g (0.00328 mol) of butylene oxide. This mixture contains 99.2% of tris-(o-tolyl)phosphine and 0.37% of tris-(o-tolyl)phosphine oxide (GC analysis).

The mixture is heated at 60° C. for 82 h. The mixture contains 98.2% of tris-(o-tolyl)phosphine and 0.53% of tris-(o-tolyl)phosphine oxide.

(b) Reaction with Pyridine N-Oxide

To a 100-mL round-bottom flask, fitted out with a magnetic stirring bar and condenser, is charged 100 g of Isopar g, 0.5 g (0.00164 mol) of tris-(o-tolyl)phosphine and 0.16 g (0.00164 mol) of pyridine N-oxide. The reaction mixture contains 35.9% of tris-(o-tolyl)phosphine and 0.34% of tris-(o-tolyl)phosphine oxide (GC analysis).

The mixture is stirred and heated at 120° C. for 64 h. The reaction mixture contains 31.9% of tris-(o-tolyl)-phosphine and 1.57% of tris-(o-tolyl)phosphine oxide.

(c) Reaction with m-Chloroperoxybenzoic Acid

To a 100-mL round-bottom flask, fitted out with a magnetic stirring bar and reflux condenser, is charged 100 g of methylene chloride, 0.5 g (0.00164 mol) of tris-(o-tolyl)phosphine and 0.28 g (0.00164 mol) of m-chloroperoxybenzoic acid. The reaction mixture contains 37.4% of tris(o-tolyl)phosphine oxide and no tris-(o-tolyl)phosphine (GC analysis). The mixture is passed through a column packed with 5 g of silica gel. GC analysis of the eluate shows that all of the tris-(o-tolyl)-phosphine oxide has been removed. The eluate is passed through a column packed with 5 g of basic alumina. GC analysis of the eluate shows that all of the m-chloroperbenzoic acid has been removed.

These experiments show that some oxidizing agents effectively convert a phosphine to a phosphine oxide. These experiments further show that a phosphine oxide can be adsorbed on silica gel and that a peroxidic oxidizing agent can be adsorbed on alumina.

EXAMPLE 7

Equimolar amounts of vinyltriacetoxysilane and 4-bromobenzocyclobutene are condensed in N-methylpyrrolidinone solvent, containing catalyst prepared from palladium (II) acetate and tris-(o-tolyl)phosphine. Triethylamine is used as hydrogen halide acceptor.

The solution of crude product is treated with cumene hydroperoxide and chromatographed over alumina. The phosphorus level of the resulting distilled product is acceptable for electronic utility.

EXAMPLE 8

(a) An experiment is run as in Example 1, using vinyltris(methoxyethoxy)silane instead of trimethoxyvinylsilane. The product is acceptable for electronic utilities.

(b) An experiment is done as in Example 5, using alpha, omega-divinyl(dimethylsiloxane) oligomer instead of 1,1'-divinyltetramethylsiloxane. Similar results are obtained.

(c) An experiment is run as in Example 1, using triacetoxyvinylsilane instead of trimethoxyvinylsilane. Similar results are obtained.

(d) An experiment is run as in Example 1, using trimethylsilylacetylene instead of trimethoxyvinylsilane. Similar results are obtained.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for purifying an impure vinylically-unsaturated organosilicon product compound prepared by reaction between a vinylically-unsaturated organosilicon precursor compound and a halogenated organic compound in the presence of a homogeneous zerovalent palladium catalyst complex, the catalyst complex including an organophosphine or organoarsine ligand, in the presence of a hydrogen halide acceptor in an essentially anhydrous diluent, comprising treating a mixture containing the impure vinylically-unsaturated organosilicon product compound with a peroxide for a time sufficient to oxidize organophosphine or organoarsine impurities present in a mixture being treated.

2. The process of claim 1, wherein the vinylically-unsaturated organosilicon precursor compound is a vinyl, ethynyl, allyl or methallyl organosilicon compound.

3. The process of claim 1, wherein the peroxide is aqueous hydrogen peroxide.

4. The process of claim 1, wherein the peroxide is an organic peroxide.

5. The process of claim 4, wherein the peroxide is tert-butyl hydroperoxide.

6. The process of claim 4, wherein the peroxide is cumene hydroperoxide.

7. The process of claim 4, wherein the peroxide is perbenzoic acid.

8. The process of claim 1, including a preliminary step of chromatographing the mixture over silica gel.

9. The process of claim 1, including a preliminary step of chromatographing the mixture over alumina.

10. The process of claim 1, including a further step of chromatographing the thus-purified compound over silica gel.

11. The process of claim 1, including a further step of chromatographing the thus-purified compound over alumina.

12. The process of claim 1, wherein the essentially anhydrous diluent comprises an organic solvent selected from the group consisting of linear and cyclic esters, alcohols, nitriles, dialkylformamides, N-alkylpyrrolidinones, alkoxyalkanols, glycol ethers, ketones, dioxane, tetrahydrofuran, tetrahydropyran or hexaalkylphosphoramides, or a mixture thereof.

13. The process of claim 12, wherein the anhydrous diluent is N,N-dimethylformamide.

14. The process of claim 12, wherein the anhydrous diluent is N-methylpyrrolidinone.

15. The process of claim 12, wherein the anhydrous diluent is acetonitrile.

16. The process of claim 1, wherein the catalyst complex is formed from a palladium salt and an organophosphine or organoarsine.

17. The process of claim 1, wherein the catalyst complex is formed from palladium (II) acetate and a triarylphosphine.

18. The process of claim 1, wherein the catalyst complex is formed from a palladium (0) complex and a triarylphosphine.

19. The process of claim 1, wherein the catalyst complex is formed from palladium (II) acetate and tris-(o-tolyl)phosphine.

20. The process of claim 1, wherein the hydrogen halide acceptor is a secondary or tertiary amine.

21. The process of claim 20, wherein the hydrogen halide acceptor is represented by the formula $R_1R_2R_3N$ and each of $R_1$, $R_2$ and $R_3$ is selected independently from straight-chain and branched-chain alkyl of 1-8 carbon atoms and cycloalkyl.

22. The process of claim 20, wherein the hydrogen halide acceptor is triethylamine.

23. The process of claim 1, wherein the halogenated organic compound is a bromo or iodo mono- or polycyclic substituted or unsubstituted carbocyclic or heterocyclic aromatic compound or a substituted or unsubstituted benzyl chloride or bromide.

24. The process of claim 1, wherein the halogenated organic compound is a brominated benzocyclobutene represented by the formula

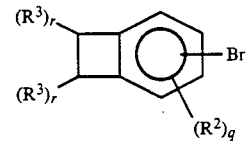

wherein $R^2$ is alkyl of 1-6 carbon atoms, alkoxy of 1-6 carbon atoms, trifluoroacetoxy, acyloxy of 1-6 carbon atoms, nitro or chloro; each $R^3$ is alkyl of 1-6 carbon atoms, aryl, nitro, chloro or cyano; q is 0, 1, 2 or 3 and each r is independently 0 or 1.

25. The process of claim 24, wherein the halogenated organic compound is 4-bromobenzocyclobutene.

26. The process of claim 1, wherein the halogenated organic compound is of the formula ArBr, wherein Ar is phenyl or o-, m- or p-tolyl.

27. The process of claim 1, wherein the halogenated organic compound is a substituted or unsubstituted benzyl chloride or bromide.

28. The process of claim 1, wherein the vinylically-unsaturated organosilicon precursor compound is a trialkoxyvinylsilane, wherein alkyl or alkoxy is of 1-6 carbon atoms.

29. The process of claim 28, wherein the trialkoxysilane is trimethoxyvinylsilane.

30. The process of claim 28, wherein the trialkoxyvinylsilane is triethoxyvinylsilane.

31. The process of claim 1, wherein the vinylically-unsaturated organosilicon precursor compound is triacetoxyvinylsilane.

32. The process of claim 1, wherein the vinylically-unsaturated organosilicon precursor compound is of the formula

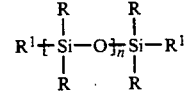

wherein each R is independently alkyl of 1-6 carbon atoms, cycloalkyl, aralkyl or aryl; each $R^1$ is independently vinyl, allyl or methallyl and n is an integer from 1 to 4500.

33. The process of claim 1, wherein the vinylically-unsaturated organosilicon precursor compound is $[CH_2=CH-Si(CH_3)_2]_2O$.

34. The process of claim 1, wherein the vinylically-unsaturated organosilicon product compound is a reaction product of 4-bromobenzocyclobutene and 1,1'-divinyltetramethyldisiloxane.

35. The process of claim 1, wherein the vinylically-unsaturated organosilicon compound is a reaction product of 4-bromobenzocyclobutene and a trialkoxyvinylsilane and alkoxy is of 1-6 carbon atoms.

36. The process of claim 35, wherein the vinylically-unsaturated organosilicon product compound is a reaction product from 4-bromobenzocyclobutene and triethoxyvinylsilane.

37. The process of claim 35, wherein the vinylically-unsaturated organosilicon product compound is a reaction product from 4-bromobenzocyclobutene and trimethoxyvinylsilane.

38. The process of claim 1, wherein the vinylically-unsaturated organosilicon product compound is a reaction product of 4-bromobenzocyclobutene and triacetoxyvinylsilane.

39. The process of claim 1, wherein the vinylically-unsaturated organosilicon product compound is a reaction product of 4-bromobenzocyclobutene and trimethoxyvinylsilane or triethoxyvinylsilane and the peroxide is aqueous hydrogen peroxide.

40. The process of claim 1, wherein the vinylically-unsaturated organosilicon product compound is a reaction product of 4-bromobenzocyclobutene and trimethoxyvinylsilane or triethoxyvinylsilane and the peroxide is tert-butyl hydroperoxide.

41. The process of claim 39, wherein the thus-purified mixture is chromatographed over silica gel or alumina.

42. The process of claim 40, wherien the thus-purified mixture is chromatographed over silica gel or alumina.

* * * * *